(12) United States Patent
Hedges et al.

(10) Patent No.: US 8,381,734 B2
(45) Date of Patent: Feb. 26, 2013

(54) PATIENT STABILIZING STRAP

(76) Inventors: Daniel Hedges, Westerville, OH (US); Jerry Faiella, Hinckley, OH (US)

(*) Notice: Subject to any disclaimer, the term of this patent is extended or adjusted under 35 U.S.C. 154(b) by 210 days.

(21) Appl. No.: 12/877,135

(22) Filed: Sep. 8, 2010

(65) Prior Publication Data
US 2011/0114102 A1 May 19, 2011

Related U.S. Application Data

(60) Provisional application No. 61/262,573, filed on Nov. 19, 2009.

(51) Int. Cl.
*A61G 15/00* (2006.01)
*A61F 5/37* (2006.01)
*A61B 19/00* (2006.01)
*A47B 7/00* (2006.01)
*A47B 1/00* (2006.01)

(52) U.S. Cl. ........ 128/845; 128/846; 128/869; 128/870; 5/621; 5/624; 5/625; 5/628

(58) Field of Classification Search .......... 128/845, 128/846, 869, 870; 5/628, 621, 624, 625
See application file for complete search history.

(56) References Cited

U.S. PATENT DOCUMENTS

| | | | |
|---|---|---|---|
| 3,297,026 A | 1/1967 | Van Pelt | |
| 3,535,719 A | 10/1970 | Murcott | |
| 4,177,807 A | 12/1979 | Ocel et al. | |
| 5,076,288 A | 12/1991 | Millard et al. | |
| 5,435,323 A * | 7/1995 | Rudy | 5/628 |
| 6,055,988 A * | 5/2000 | Perisho | 128/869 |

\* cited by examiner

*Primary Examiner* — Justine Yu
*Assistant Examiner* — Nihir Patel
(74) *Attorney, Agent, or Firm* — Tarolli, Sundheim, Covell & Tummino LLP

(57) ABSTRACT

A patient stabilizing strap includes a base strap, which is removably attachable to a planar surface. At least one receiving portion is secured to the planar surface by the base strap. At least one elongate stabilizing portion has longitudinally spaced first and second stabilizing portion ends separated by a stabilizing portion body. Each first stabilizing portion end is removably attachable to a receiving portion to secure the stabilizing portion to the planar surface. Each second stabilizing portion end is removably attachable to an other second stabilizing portion end to encircle at least a portion of a patient body in cooperation with the planar surface.

15 Claims, 4 Drawing Sheets

PATIENT STABILIZING STRAP

RELATED APPLICATION

This application claims priority from U.S. Provisional Application No. 61/262,573, filed Nov. 19, 2009, the subject matter of which is incorporated herein by reference.

TECHNICAL FIELD

The present invention relates to an apparatus and method for use of a patient stabilizing strap and, more particularly, to a method of, and system for, stabilizing a human body on a planar surface.

BACKGROUND OF THE INVENTION

When a patient in a medical setting is partially sedated, he or she may find it difficult to maintain balance or body position. This is particularly problematic when the patient is lying atop a narrow, possibly mobile, surface. For example, a semi-medicated patient resting on a narrow exam table during a catheterization or imaging procedure, or being moved between rooms on a gurney, may have an increased propensity to change position unexpectedly or even fall because of impaired reflexes caused by his or her sedated condition. Additionally, a patient under the influence of a sedative could easily forget that he or she is supposed to be lying still for a medical test or procedure and attempt to rise or shift position in a way which might jeopardize the accuracy or integrity of the medical procedure.

The National Quality Forum ("NQF"), a nonprofit group in Washington, DC dedicated to setting health care quality standards, considers falls to be one of 28 serious reportable adverse patient care events included in a list used by many states to set patient care standards. In 2008, following a 2006 NQF study including this classification for falls, the U.S. Department of Health and Human Services indicated that Medicare/Medicaid would no longer pay for treatment of injuries incurred by a patient through a fall in a healthcare facility. Because of the nonreimburseable costs involved with caring for these fall-injured patients, health care providers have an additional incentive to avoid loss of balance events during medical treatment.

Therefore, it is desirable to provide a method and apparatus which can help to stabilize at least a portion of the patient's body and provide the patient with a sense of physical security when the patient's reflexes are impaired.

SUMMARY OF THE INVENTION

In an embodiment of the present invention, a patient stabilizing strap is described. A base strap is removably attachable to a planar surface. At least one receiving portion is secured to the planar surface by the base strap. At least one elongate stabilizing portion has longitudinally spaced first and second stabilizing portion ends separated by a stabilizing portion body. Each first stabilizing portion end is removably attachable to a receiving portion to secure the stabilizing portion to the planar surface. Each second stabilizing portion end is removably attachable to an other second stabilizing portion end to encircle at least a portion of a patient body in cooperation with the planar surface.

In an embodiment of the present invention, a method of stabilizing a human body on a planar surface is provided. A base strap is removably attached to the planar surface. At least one receiving portion is secured to the planar surface with the base strap. At least one elongate stabilizing portion having longitudinally spaced first and second stabilizing portion ends separated by a stabilizing portion body is provided. The stabilizing portion is secured to the planar surface by removably attaching each first stabilizing portion end to a receiving portion. Each second stabilizing portion end is removably attached to an other second stabilizing portion end. At least a portion of a patient body is encircled with the attachment of the second stabilizing portion end to the other second stabilizing portion end in cooperation with the planar surface.

In an embodiment of the present invention, a system for stabilizing a human body on a planar surface is described. The planar surface has oppositely disposed and laterally spaced longitudinal edges. A base strap is removably attached to the planar surface. First and second receiving portions are secured to the planar surface by the base strap. Each of the first and second receiving portions is located adjacent one of the longitudinal edges. First and second stabilizing portions having longitudinally spaced stabilizing portion ends separated by a stabilizing portion body are provided. Each of the first and second stabilizing portions has one stabilizing portion end removably attached to one of the first and second receiving portions. Each of the first and second stabilizing portions has an other stabilizing portion end removably attachable to the other of the first and second stabilizing portions to selectively form at least a portion of an encircling cincture in cooperation with the planar surface. The human body is located within the cincture and is selectively urged toward a stable position upon the planar surface by at least one of the base strap, first and second receiving portions, and first and second stabilizing portions.

BRIEF DESCRIPTION OF THE DRAWINGS

For a better understanding of the invention, reference may be made to the accompanying drawings, in which.

DESCRIPTION OF EMBODIMENTS

Figure 1:
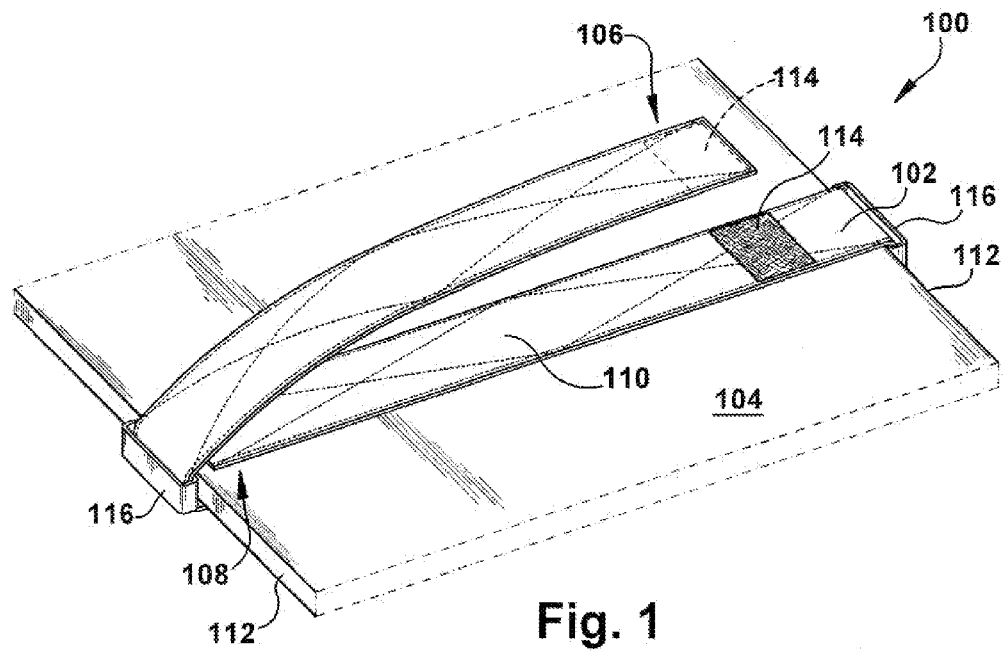
FIG. 1 is a partial perspective view of one embodiment of the present invention.

In accordance with the present invention, FIG. 1 depicts a patient stabilizing strap 100. A base strap 102 is removably attachable to a planar surface 104. The planar surface 104 may be a patient-supporting surface, such as a gurney, backboard, or catheterization table, or may be a surface which is merely located adjacent, and not necessarily supporting, the patient. The term "planar" is used herein to indicate a surface which generally has a two-dimensional quality such as the planar surface 104 shown, but this definition is broad enough to include surfaces which are not strictly located entirely within a single plane. For example, a "planar surface" may include protruding legs or wheels on an underside thereof without destroying the planar nature of the patient-facing side of that planar surface. The patient stabilizing strap 100 may be provided along with a new planar surface 104 or may be retrofitted to an existing planar surface 104.

The base strap 102 may have a first base strap end 106 and a second base strap end 108, longitudinally separated by a base strap body 110. The base strap 102 may be secured to the planar surface 104 in any suitable manner. For example, and as shown herein, the base strap body 110 is wrapped around the planar surface 104, contacting each of two oppositely disposed and laterally spaced longitudinal edges 112 of the planar surface 104. The second base strap end 108 then lies upon the planar surface 104 while the first base strap end 106 is laid atop, and secured to, a portion of the base strap body 110 using one or more fasteners, shown generally at 114. In this manner, the base strap 102 may be attached to the planar surface 104 in an encircling manner.

These fasteners 114 may be located on one or both sides of the base strap 102 and may be of any suitable type, including, but not limited to, snaps, temporary or permanent adhesives, sewn connections, buttons, zippers, or the like, but will be shown and described herein as being areas of appropriately positioned and configured hook and loop fasteners, such as those commercially sold under the brand name Velcro® by Velcro USA, Inc., of Manchester, N.H., USA. A fastener 114 patch in FIG. 1 is shown schematically as being on a top surface of the first base strap end 106, but this depiction is provided for ease of description. One of ordinary skill in the art can readily provide a suitable number, location, and type of fasteners for a particular application of the present invention.

It is contemplated that, particularly when the planar surface 104 has a relatively constant cross-section, the base strap 102 need not have first and second base strap ends 106 and 108, but could instead be a closed loop (not shown) of material and could be slid longitudinally into a desired location from an end (not shown) of the planar surface 104. While a direct attachment to the planar surface 104 is possible, it is contemplated that, for most applications of the present invention, the base strap 102 can be attached to the planar surface 104 in a noninvasive and reversible manner, so that the planar surface is minimally effected, if at all, by the presence of the patient stabilizing strap 100.

At least one receiving portion 116 is secured to the planar surface 104 by the base strap 102. As shown here, the receiving portion 116 may be simply a loop of material at least partially surrounding the base strap body 110. One of ordinary skill in the art can readily provide a receiving portion 116 configured for use as described below for a particular application of the present invention. The receiving portion 116 is optionally attached to the base strap 102.

Figure 2:
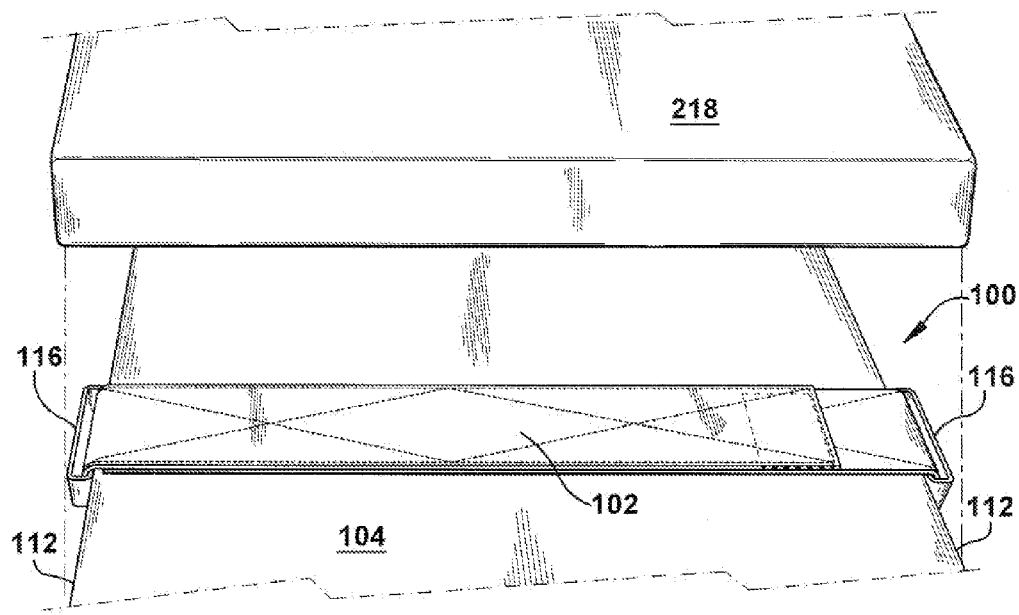
FIG. 2 is a partial top view of the embodiment of FIG. 1.

FIG. 2 depicts a partial top view of the patient stabilizing strap 100, wherein the base strap 102 has been attached to the planar surface 104 and a plurality of receiving portions 116 (two shown here as first and second receiving portions) are being secured to the planar surface 104 by the base strap. Each of the first and second receiving portions is located adjacent one of the longitudinal edges 112. As shown in FIG. 2, an intermediate surface 218 may be provided and may be placed atop the planar surface 104, optionally sandwiching at least a portion of the base strap 102 therebetween. While the intermediate surface 218 shown here is a padded structure, such as a foam slab or mattress, the intermediate surface 218 could be a sanitizing drape or other cloth or plastic sheet having any desired flexibility.

Though the intermediate surface 218 is shown in FIG. 2 as being present on a portion of the planar surface 104 spaced apart from the base strap 102, the intermediate surface could also or instead cover the base strap (thus hiding it from view in the orientation of FIG. 2) for sanitary, comfort, prevention of access, and/or any other reasons or combination of reasons. When a patient is being supported by the planar surface 104, as will be discussed shortly, the intermediate surface 218 can be interposed between the base strap 102 and the patient's body.

Figure 3:
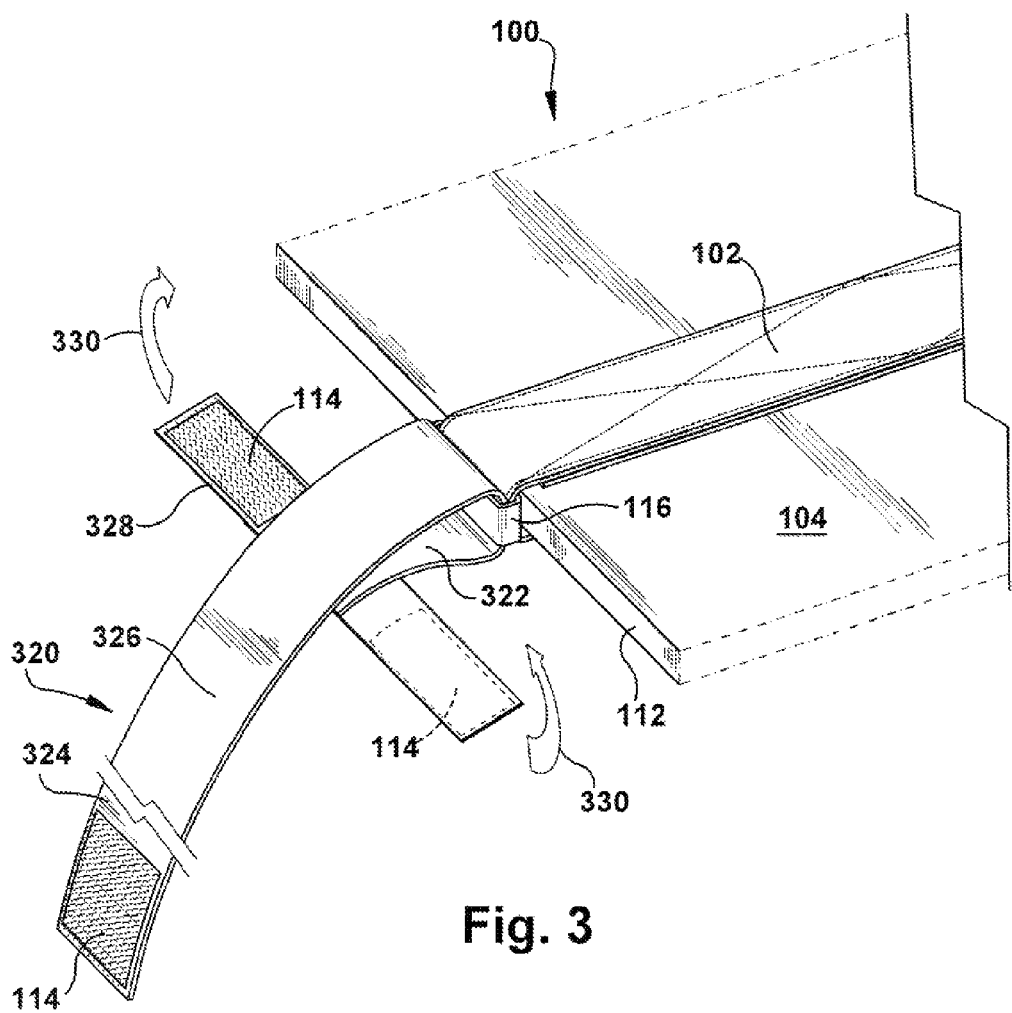
FIG. 3 is a partial side view of the embodiment of FIG. 1.

Turning to FIG. 3, an elongate stabilizing portion 320 is shown being attached to one of the receiving portions 116. The stabilizing portion 320, which comprises a part of the patient stabilizing strap 100, has longitudinally spaced first and second stabilizing portion ends 322 and 324, respectively, separated by a stabilizing portion body 326. The first stabilizing portion end 322 is removably attachable to one of the receiving portions 116 to secure the stabilizing portion 320 to the planar surface 104. The attachment of the first stabilizing portion end 322 to a receiving portion 116 could be accomplished in any suitable manner, and one of ordinary skill in the art can readily provide appropriate fasteners for a particular fastening/connection scheme. One example of a suitable fastening arrangement is shown in FIG. 3.

In FIG. 3, more particularly, the first stabilizing portion end 322 includes a lateral securing strap 328. The stabilizing portion 320 is attached to the receiving portion 116 by the stabilizing portion body 326 being passed through and held by the receiving portion 116, as shown. The lateral securing strap 328 can then be fastened laterally around the stabilizing portion body 326 to prevent the stabilizing portion body from exiting the receiving portion 116. For example, the lateral securing strap 328 can include one or more fasteners 114, with the ends of the lateral securing strap 328 being folded inward (as shown by direction arrows 330) to bring the fasteners 114 into engagement and thereby secure the stabilizing portion 320 in the depicted position. The fastening arrangement of FIG. 3 provides for a rotatable, "hinged" relationship between the stabilizing portion 320 and the receiving portion 116, which may be desirable in certain applications of the present invention.

Figure 4:
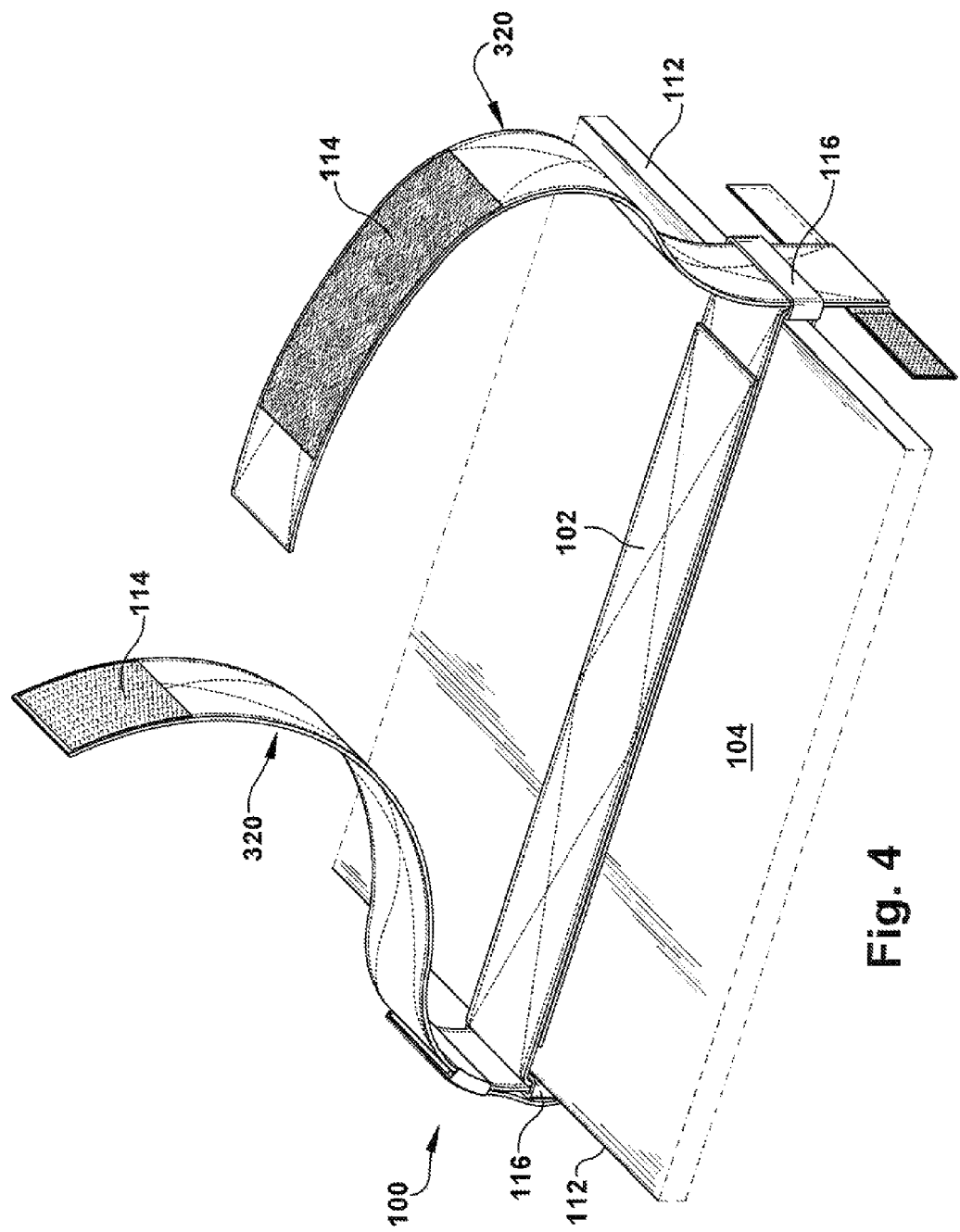
FIG. 4 is a perspective view of the embodiment of FIG. 1.

FIG. 4 shows a substantially complete patient stabilizing strap 100, having a base strap 102 secured to a planar surface 104 and a plurality of stabilizing portions 320 (here, two), with each stabilizing portion attached to a different receiving portion 116 (one stabilizing portion shown unfastened here, partially through the attachment process). While the receiving portions 116 are shown in FIG. 4 as being located at the longitudinal edges 112 of the planar surface 104, any number of receiving portions 116 could be provided to a single base strap 102, and located in any desired position thereupon. Each stabilizing portion 320 has a fastener 114 located thereupon, and the fasteners 114 facilitate connection of multiple stabilizing portions together.

Figure 5:
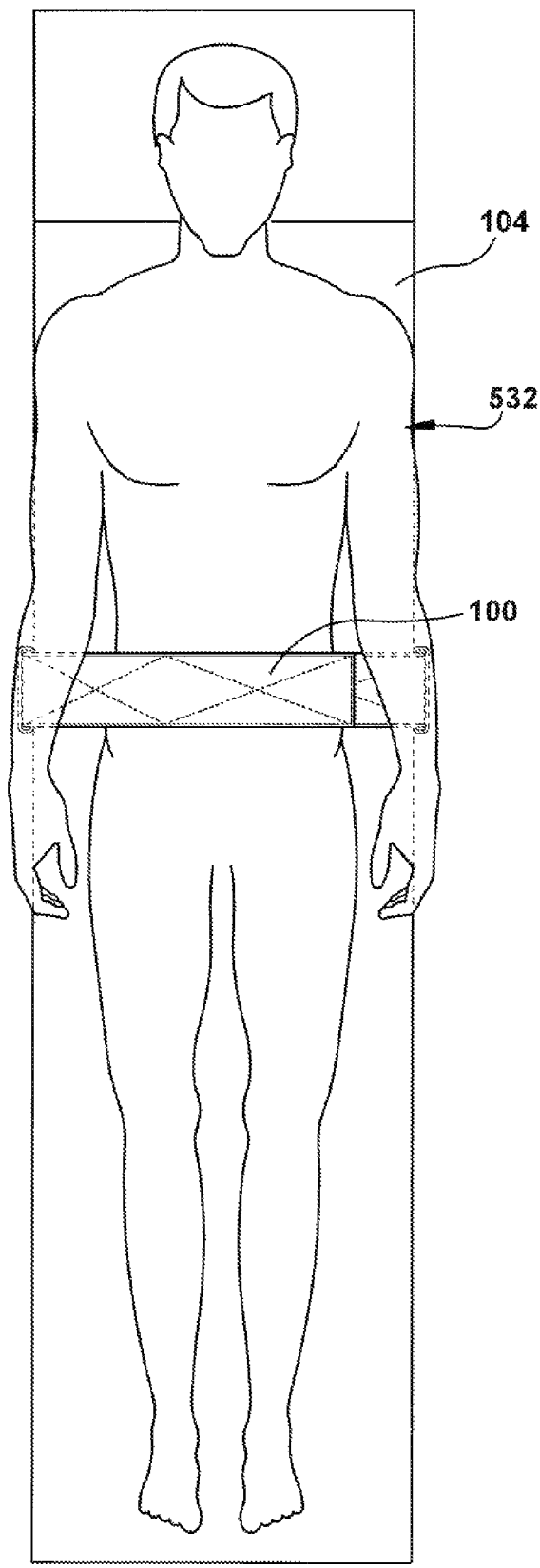
FIG. 5 is a top view of the embodiment of FIG. 1 in an example use environment.

FIG. 5 depicts a patient 532 lying atop the planar surface 104 and being stabilized in that position by the patient stabilizing strap 100. The patient 532 is lying atop the base strap (102, not visible in FIG. 5). As previously mentioned, an intermediate surface (218, omitted from FIG. 5) could be interposed between the base strap 102 and the patient 532 for comfort, sterility, or any other reason.

In the use position of FIG. 5, the stabilizing portions 320 have been attached together across a torso of the patient 532 to encircle at least the torso portion of the patient's body, in cooperation with the planar surface 104. This removable attachment may be accomplished in any suitable manner. For example, a second stabilizing portion end 324 of one stabilizing portion 320 attached to a first receiving portion 116 may be attached to an other second stabilizing portion end 324 of an other stabilizing portion 320 attached to a second receiving portion 116, such as in the arrangement shown in FIG. 4. Optionally, there is some overlap between the two stabilizing portions 320 being attached together, in order to provide a desired amount of relative fastening force—hook and loop fasteners, for example, may require that at least a certain predetermined amount of surface area of the stabilizing portions 320 be in contact for desired attachment.

Regardless of the manner in which the stabilizing portions 320 are attached, however, an encircling cincture is formed about at least a portion of the patient's 532 body when the patient stabilizing strap 100 is in the use environment and configuration of FIG. 5. When the patient 532 is at least partially located within the cincture as desired, the encircled portion of the patient's body is urged toward a stable position upon the planar surface 104 by at least one of the base strap 102, the receiving portions 116, and the stabilizing portions 320.

The patient stabilizing strap 100 may be integrally formed or assembled from separate components, and each component may be made of any suitable material or combination of materials. For example, at least one of the base strap 102, the receiving portions 116, and the stabilizing portions 320 may be formed from a flat ribbon or strip of a durable, flexible material. One example of a suitable material is ballistic nylon. The dimensions, thickness, and other physical characteristics of the material used may depend upon which of the base strap 102, the receiving portions 116, and the stabilizing portions 320 is being made of that particular material. The material(s) used for various structures of the patient stabilizing strap may be treated or impregnated with an antibacterial, waterproofing, or other desired treatment. In certain applications of the present invention, it may be desirable for part or all of the patient stabilizing strap 100 to be made from radiolucent (partly or wholly permeable to radiation) materials. For example, when the planar surface 104 is a radiograph table, the patient stabilizing strap 100 should be made of materials that will not show up on a patient's radiographs.

The attachments of the base strap 102 to the planar surface 104, the first stabilizing portion end 322 to the receiving portion 116, and the second stabilizing portion end 324 to an other second stabilizing portion end 324 may be accomplished using any suitable fastener, but is shown and described herein as being aided by a hook and loop fastener.

Though the stabilizing portion 320 and the receiving portion 116 can be attached in any suitable manner, permanent or temporary, it is contemplated that the stabilizing portion(s) 320 of the patient stabilizing strap 100 (and possibly also the receiving portion(s) 116) may undergo more wear and patient contact than the base strap 102. Therefore, it may be desired in some applications of the present invention that the stabilizing portion(s) 320 and/or the receiving portion(s) 116 can be fastened firmly to the base strap 102 for use but be relatively easily removable for replacement with a different stabilizing portion(s) and/or receiving portion(s), as desired. Such selective replacement of at least one of the base strap 102, receiving portions 116, and/or stabilizing portions 320 with another such component may be made responsive to at least one of wear magnitude, desired dimensions, desired material, and desired fastener of the replacing base strap, receiving portion, and/or stabilizing portion, as appropriate. For example, regardless of whether a stabilizing portion 320 is worn out, it may be desirable for a longer, wider, freshly sterilized, and/or more padded replacement stabilizing portion to be provided instead, for a single patient 532 use or on an ongoing basis. It is contemplated that a variety of base straps 102, receiving portions 116, and/or stabilizing portions 320 could be stocked and substituted as desired. Alternately, and more simply, a plurality of substantially similar stabilizing portions 320 could be stocked to replace the existing stabilizing portions when needed for wear reasons. Since hook and loop fasteners generally become less effective over time, it may be desirable for the stabilizing portions 320 (the fasteners 114 of which are manipulated with every patient 532) to be easily replaceable, while a single base strap 102 (the fasteners 114 of which would likely be manipulated much less often than with every patient 532) could remain in service through the lifetime of multiple replacement stabilizing portions 320.

While aspects of the present invention have been particularly shown and described with reference to the preferred embodiment above, it will be understood by those of ordinary skill in the art that various additional embodiments may be contemplated without departing from the spirit and scope of the present invention. For example, the disclosed invention could be used for restraining movement of a human body, and one of ordinary skill in the art could readily enhance the described components sufficiently to hold a resisting person in a desired position. Multiple patient stabilizing straps 100 could be located in several places on a single planar surface 104. A sterile sleeve (not shown) could be provided to sheathe the stabilizing portion(s) 320 to facilitate quick turnaround of the planar surface 104 for use by another patient. A relatively small portion of the patient's body, such as a single limb, could be encircled by the patient stabilizing strap 100, in which case the planar surface 104 may be, for example, an arm- or legboard rather than a surface which supports the patient's entire body. A variety of fastener 114 options (e.g., a plurality of fastener 114 areas having male and/or female fastening portions provided to a single component) could be provided to allow the user to attach the structures of the patient stabilizing strap 100 together in various embodiments. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. A patient stabilizing strap, comprising:
   a base strap, removably attachable to a planar surface;
   at least one receiving portion secured to the planar surface by the base strap; and
   at least one elongate stabilizing portion having longitudinally spaced first and second stabilizing portion ends separated by a stabilizing portion body, each first stabilizing portion end being removably attachable to a receiving portion to secure the stabilizing portion to the planar surface, and each second stabilizing portion end being removably attachable to an other second stabilizing portion end to encircle at least a portion of a patient body in cooperation with the planar surface; and
   wherein the first stabilizing portion end includes a lateral securing strap, and the stabilizing portion is attached to the receiving portion by the stabilizing portion body being passed through and held by the receiving portion and the lateral securing strap being fastened laterally around the stabilizing portion body to prevent the stabilizing portion body from exiting the receiving portion.

2. The patient stabilizing strap of claim 1, wherein at least one of the attachments of the base strap to the planar surface, the first stabilizing portion end to the receiving portion, and the second stabilizing portion end to an other second stabilizing portion end is aided by a hook and loop fastener.

3. The patient stabilizing strap of claim 1, wherein at least one of the base strap, the receiving portion, and the stabilizing portion is formed from a flat ribbon of a durable, flexible material.

4. The patient stabilizing strap of claim 1, wherein the patient body is supported by the planar surface.

5. The patient stabilizing strap of claim 1, including a intermediate surface interposed between the base strap and the patient body.

6. The patient stabilizing strap of claim 1, wherein the base strap encircles the planar surface when attached thereto.

7. A method of stabilizing a human body on a planar surface, the method comprising the steps of:
removably attaching a base strap to the planar surface;
securing at least one receiving portion to the planar surface with the base strap;
providing at least one elongate stabilizing portion having longitudinally spaced first and second stabilizing portion ends separated by a stabilizing portion body;
securing the stabilizing portion to the planar surface by removably attaching each first stabilizing portion end to a receiving portion;
removably attaching each second stabilizing portion end to an other second stabilizing portion end;
encircling at least a portion of a patient body with the attachment of the second stabilizing portion end to the other second stabilizing portion end in cooperation with the planar surface;
providing the first stabilizing portion end with a lateral securing strap;
passing the stabilizing portion body through the receiving portion;
holding the stabilizing portion body within the receiving portion; and
preventing the stabilizing portion body from exiting the receiving portion by laterally fastening the lateral securing strap around the stabilizing portion body.

8. The method of claim 7, including the step of aiding at least one of the attachments of the base strap to the planar surface, the first stabilizing portion end to the receiving portion, and the second stabilizing portion end to an other second stabilizing portion end with a hook and loop fastener.

9. The method of claim 7, including the step of forming at least one of the base strap, the receiving portion, and the stabilizing portion from a flat ribbon of a durable, flexible material.

10. The method of claim 7, including the step of supporting the patient body with the planar surface.

11. The method of claim 7, including the step of interposing a intermediate surface between the base strap and the patient body.

12. The method of claim 7, including the step of encircling the planar surface with the base strap.

13. A system for stabilizing a human body on a planar surface, the planar surface having oppositely disposed and laterally spaced longitudinal edges, the system comprising:
a base strap removably attached to the planar surface;
first and second receiving portions secured to the planar surface by the base strap, with each of the first and second receiving portions located adjacent one of the longitudinal edges; and
first and second stabilizing portions having longitudinally spaced stabilizing portion ends separated by a stabilizing portion body, each of the first and second stabilizing portions having one stabilizing portion end removably attached to one of the first and second receiving portions, and each of the first and second stabilizing portions having an other stabilizing portion end removably attachable to the other of the first and second stabilizing portions to selectively form at least a portion of an encircling cincture in cooperation with the planar surface; wherein
the human body is located within the cincture and is selectively urged toward a stable position upon the planar surface by at least one of the base strap, first and second receiving portions, and first and second stabilizing portions; and wherein
at least one stabilizing portion end includes a lateral securing strap, and at least one stabilizing portion end is removably attached to one of the first and second receiving portions by the respective stabilizing portion body being passed through and held by the respective receiving portion and the lateral securing strap being fastened laterally around the respective stabilizing portion body to prevent the stabilizing portion body from exiting the receiving portion.

14. The system of claim 13, wherein at least one of the base strap, first and second receiving portions, and first and second stabilizing portions is selectively replaced by another base strap, first or second receiving portion, or first or second stabilizing portion, respectively, responsive to at least one of wear magnitude, desired dimensions, desired material, and desired fastener of the replacing base strap, first or second receiving portion, or first or second stabilizing portion.

15. The system of claim 13, wherein at least one of the attachments of the base strap to the planar surface, the first and second receiving portions to the base strap, the stabilizing portion end to one of the first and second receiving portions, and the other stabilizing portion end to the other of the first and second stabilizing portions is aided by a hook and loop fastener.

* * * * *